United States Patent [19]

Rontome et al.

[11] Patent Number: 5,384,091
[45] Date of Patent: Jan. 24, 1995

[54] METHOD AND DEVICE FOR DISINFECTING CONTACT LENSES

[75] Inventors: Carlo P. Rontome; Santiag N. Padilla, both of Madrid, Spain

[73] Assignee: Dirygesa, S.A., Madrid, Spain

[21] Appl. No.: 10,488

[22] Filed: Jan. 28, 1993

Related U.S. Application Data

[63] Continuation of Ser. No. 695,317, May 3, 1991, abandoned.

[30] Foreign Application Priority Data

May 3, 1990 [ES] Spain ................................. 9001251

[51] Int. Cl.6 ........................................ A61L 2/16
[52] U.S. Cl. ........................................ 422/30; 422/28; 422/300; 422/301
[58] Field of Search ............. 134/901; 206/5.1; 422/28, 30, 300, 301, 292, 263, 264, 265; 220/408, 409, 410

[56] References Cited

U.S. PATENT DOCUMENTS

| Re. 32,672 | 5/1988 | Huth et al. ................ | 514/840 |
|---|---|---|---|
| 5,05,402 | 10/1991 | Seamons et al. .......... | 422/300 |
| 1,272,222 | 7/1918 | Clayton .................... | 220/409 |
| 3,586,012 | 6/1971 | Paule ....................... | 134/93 |
| 4,106,486 | 8/1978 | Lee .......................... | 220/409 |
| 4,217,331 | 8/1980 | Schaub ..................... | 422/264 |
| 4,822,579 | 4/1989 | Wagner ..................... | 422/665 |
| 5,011,661 | 4/1991 | Schäfer et al. ............ | 422/30 |
| 5,064,624 | 11/1991 | King ......................... | 422/265 |
| 5,086,952 | 2/1992 | Kryk ........................ | 422/264 |

*Primary Examiner*—Robert J. Warden
*Assistant Examiner*—T. A. Trembley
*Attorney, Agent, or Firm*—Collard & Roe

[57] ABSTRACT

A method and device for disinfecting an item with a disinfecting agent and a suitable neutralizer to neutralize the agent. The item is placed in a container with the agent. A neutralizer is placed in the container in a receptacle which hinders the contact between the agent and the neutralizer so that the items can be disinfected. A device includes a container and a receptacle which regulates the renewal of the agent in contact with the neutralizer.

4 Claims, 1 Drawing Sheet

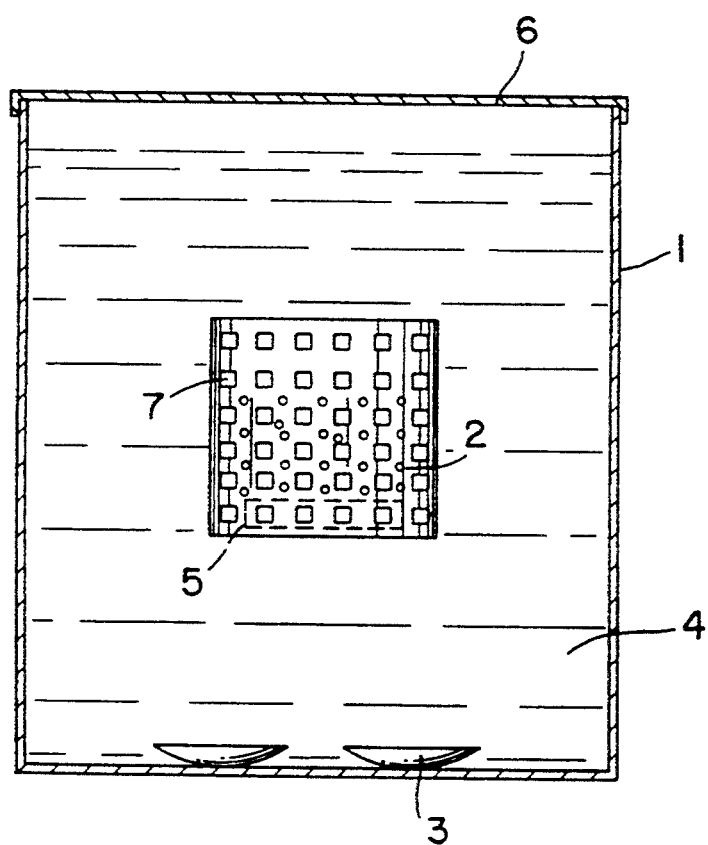

METHOD AND DEVICE FOR DISINFECTING CONTACT LENSES

This is a continuation of copending application Ser. No. 07/695,317 filed on may 3, 1991, now abandoned.

BACKGROUND OF THE INVENTION

1. Field of the Invention

The present invention relates to a method and device for disinfecting and cleaning contact lenses and other small items. More particularly, the method consists of inserting the item to be disinfected into a container which contains hydrogen peroxide ($H_2O_2$) for disinfecting and a reducing agent. The reducing agent is placed in a perforated or slotted receptacle, for example. The receptacle constitutes a physical barrier which delays the action of the reducing agent until the $H_2O_2$ has disinfected and cleaned the item.

2. The Prior Art

Contact lenses, during use, acquire various grease, protein or other deposits. These deposits serve as a substrate for ambient microorganisms which can damage the lens or injure the eye. As a result, various methods have been conceived to disinfect contact lenses. These methods utilize $H_2O_2$, which has strong disinfecting power without damaging the morphology of the lens.

Nevertheless, the use of $H_2O_2$ presents a problem in that a residue of this substance on a lens may produce serious irritation of the eye. Thus, conventional procedure consists of first disinfecting the lens with $H_2O_2$ in a suitable container and, once disinfected, neutralizing the $H_2O_2$. This can be accomplished by various known methods, e.g., chemical compounds, catalysts, clarifiers with salt water, etc. In this manner, the concentration of peroxide in solution is reduced to levels that do not irritate the eye. Obviously, this two-step method is time-consuming and may be harmful if the user neglects a step.

To overcome these disadvantages, other methods have subsequently been developed which are based on disinfecting and neutralizing in a single step. The lens is inserted into a container which contains both $H_2O_2$ and other products necessary for reducing the $H_2O_2$ and providing a solution suitable for maintaining the lens. These methods delay the reducing action, by means of coatings that dissolve after a certain time. These substances may include various forms of galenical preparations. These preparations are described in Spanish patent number 86/01791 to Ciba-Geigy AG.

Other single-step methods involve reducing the $H_2O_2$ with heavy metal catalysts, such as platinum. In addition to providing slow reduction, the catalytic effect is diminished as the peroxide concentration decreases.

Whatever procedure is used, the concentration of peroxide should be sufficiently high for a period of time necessary to disinfect.

SUMMARY OF THE INVENTION

It is therefore an object of the present invention to eliminate the aforementioned drawbacks of the prior art and to provide a method to safely and quickly disinfect contact lenses.

It is also an object of the present invention to provide a device to safely and quickly disinfect contact lenses.

These and other related objects are attained according to the invention by a method where $H_2O_2$ and a reducing agent are combined in a single container. The effect of the neutralizer is delayed by simple means so that $H_2O_2$ maintains an effective concentration level for a sufficient time. At the end of the process, the concentration of peroxides is reduced so that the residual peroxide is at a safe level.

More specifically, the method of the invention utilizes a container in which the neutralizer is placed, either in tablet, capsule or any other galenical form, even liquid. The receptacle is then placed in the disinfecting container with the $H_2O_2$. The receptacle can be formed as part of the container and having a perforated or slotted cover. The receptacle or cover is designed to constitute a physical impediment which hinders contact between $H_2O_2$ and the reducing agent or neutralizer. The receptacle and container are also part of the invention. The holes or cracks impede the escape of the bubbles released in the neutralizer-oxygenated water reaction by the release of oxygen. In addition, the renewal of the solution in contact with the reducing agent is delaying the process for a time sufficient to achieve complete disinfection. The reaction can be regulated based on the number and configuration of the openings.

BRIEF DESCRIPTION OF THE DRAWINGS

Other objects and features of the present invention will become apparent from the following detailed description considered in connection with the accompanying drawing which discloses one embodiment of the present invention. It should be understood, however, that the drawing is designed for the purpose of illustration only and not as a definition of the limits of the invention.

The FIGURE is a cross-sectional view of the container and receptacle contained therein embodying the present invention.

DETAILED DESCRIPTION OF PREFERRED EMBODIMENTS

Referring now in detail to the FIGURE, there is shown a container 1 and a perforated receptacle 2 containing the reducing agent. Receptacle 2 may be of any configuration. The procedure for disinfecting contact lenses is carried out basically by means of two substances. The first is an aqueous solution of hydrogen peroxide ($H_2O_2$), preferably 0.5% to 3% by weight. The $H_2O_2$ disinfects the lens to eliminate any type of microorganism deposited thereon. The second is a reducing agent which is an enzymatic catalyst, preferably catalase. The reducing agent can be in tablet, capsule or any other galenical form. The reducing agent can be the sole component thereof or combined with other additional substances.

Thus, the procedure for disinfecting contact lenses consists of inserting a lens 3 into a container 1, which contains an aqueous solution of $H_2O_2$ for the disinfection of lens 3. Receptacle 2 is provided with a tablet 5 of the reducing agent. Container 1 is closed by means of a lid 6. Initially, a part of the $H_2O_2$ solution 4 penetrates through orifices 7 of receptacle 2 and, upon contact with reducing agent 5, oxygen is released. Bubbles 8 are formed which, upon release, try to escape through orifices 7 in receptacle 2. The surface tension of the solution around orifices 7 prevents the gas bubbles from escaping until its pressure is greater than the surface tension. Receptacle 2 acts as a physical impediment and in addition bubbles 8 plug orifices 7 such that they prevent any more $H_2O_2$ solution 4 from coming into contact with reducing agent 5. Also, receptacle 2 prevents rapid convection and thereby hinders the renewal of $H_2O_2$ solution 4 in contact with reducing agent 5.

Thus, in a first step, there is a period in which a great quantity of $H_2O_2$ 4 is not yet reduced and can act as a disinfectant on lens 3. The disinfection time is easily regulated by calculating the size of orifices 7 and their number. Once the disinfection is complete, reducing agent 5 continues reacting with the remaining $H_2O_2$, reducing it until the peroxide concentration in the solution is lowered to levels that are not harmful for the eye that will receive the lens. This level is approximately less than 50 ppm.

Other substances which easily dissolve may be added to the solution or to the tablets or capsules 5. These substances, for example, can be substances which bring the final solution to a neutral pH. Thus, the solution will match the pH of the tears of the eye. These substances are, for example, boric acid and borax, monosodium phosphate and disodium phosphate, tartaric acid and sodium carbonate or bicarbonate, and citric acid and sodium carbonate or bicarbonate. They may also include substances which affect the osmotic pressure, to adjust it to approximately 300 m Os, for example, sodium chloride, potassium chloride or sodium edetate.

Because all these components are added at the same time, it is not necessary to open the container during the disinfection process. Therefore, it has the additional advantage of not having to add any chemical preservative to the solution (such as thimerosal, chlorhexidine hydrochloride) which often produce hypersensitivity of the eye.

Receptacle 2, in which reducing agent 5 is placed, can be designed in many different ways. Thus, it can be part of container 1 or an independent element. It can also be provided as the receptacle in which the neutralizer is sold.

Although this procedure is designed primarily for disinfecting contact lenses, it may be used to disinfect other small items which require cleaning of similar microorganisms.

The method is advantageous over known methods, since known methods require two or more steps for disinfection and subsequent reduction. The method of the invention is much more convenient, rapid, simple to use and safe and is just as effective as any other method.

While only one embodiment of the present invention has been shown and described, it is to be understood that many changes and modifications may be made thereunto without departing from the spirit and scope of the invention as defined in the appended claims.

What is claimed is:

1. A method for disinfecting a contact lens with a disinfectant and later neutralizing the disinfectant, comprising the steps of:
   providing a container containing a hydrogen peroxide disinfectant;
   placing a contact lens to be disinfected into the container containing the hydrogen peroxide disinfectant;
   providing a receptacle with openings therein, the receptacle being separate from the container;
   placing a reducing agent, a pH adjusting agent and an osmotic pressure adjusting agent into the receptacle, the reducing agent being selected from the group consisting of an enzymatic catalyst, and catalase, the pH adjusting agent being selected from the group consisting of boric acid and borax, tartaric acid and sodium bicarbonate, citric acid and sodium carbonate, and citric acid and sodium bicarbonate, and the osmotic pressure adjusting agent being selected from the group consisting of potassium chloride, and sodium edetate; and
   placing the receptacle with the reducing agent, the pH adjusting agent and the osmotic pressure adjusting agent into the container, the receptacle serving as a physical barrier between the hydrogen peroxide disinfectant and reducing agent, the number and configuration of the openings preventing a gaseous reduction process product from escaping from the receptacle until the pressure inside the receptacle is greater than the surface tension at the openings, thus delaying the reduction of the hydrogen peroxide disinfectant until the contact lens is disinfected.

2. The method as claimed in claim 1, wherein the reducing agent is in a form selected from the group consisting of a tablet, a capsule, a liquid, and galenical form.

3. A device for disinfecting a contact lens with a disinfectant and later neutralizing the disinfectant, comprising:
   a container with a lid for containing a contact lens and a hydrogen peroxide disinfectant;
   a receptacle having openings therein, the receptacle being separate from said container and located within said container for receiving a reducing agent, a pH adjusting agent and an osmotic pressure adjusting agent, said receptacle serving as a physical barrier between the hydrogen peroxide disinfectant and the reducing agent for delaying the reduction of the hydrogen peroxide disinfectant until the contact lens is disinfected; the reducing agent is selected from the group consisting of an enzymatic catalyst and catalase, the pH adjusting agent is selected from the group consisting of boric acid and borax, tartaric acid and sodium bicarbonate, citric acid and sodium carbonate, citric acid and sodium bicarbonate, the osmotic pressure adjusting agent is selected from the group consisting of potassium chloride, and sodium edetate; and
   wherein said openings are of a predetermined number, each having a predetermined configuration, the hydrogen peroxide disinfectant and reducing agent combining to form gas bubbles within said receptacle that block the openings, thereby limiting the combining of the hydrogen peroxide disinfectant and the reducing agent so as to regulate the reduction of the hydrogen peroxide disinfectant; and
   wherein the predetermined number of openings and predetermined configuration of the openings establish a particular surface tension at each opening between the gas bubbles formed within said receptacle and the hydrogen peroxide disinfectant disposed outside said receptacle, wherein the gas bubbles are prevented from exiting said receptacle until the pressure inside said receptacle is greater than the surface tension at each opening.

4. A method for disinfecting a contact lens, comprising the steps of
   providing a container containing hydrogen peroxide in aqueous solution;

placing contact lens to be disinfected into the container containing the hydrogen peroxide in aqueous solution;

providing a perforated receptacle that is separate from the container;

placing a reducing agent, a pH adjusting agent and an osmotic pressure adjusting agent into the perforated receptacle, the reducing agent being selected from the group consisting of an enzymatic catalyst and catalase, the pH adjusting agent being selected from the group consisting of boric acid and borax, tartaric acid and sodium bicarbonate, citric acid and sodium carbonate and citric acid and sodium bicarbonate, and the osmotic pressure adjusting agent being selected from the group consisting of potassium chloride, and sodium edetate;

placing the perforated receptacle containing the reducing agent, the pH adjusting agent and the osmotic pressure adjusting agent into the container, the reducing agent and the hydrogen peroxide disinfectant combining and forming bubbles, which block the perforations and inhibits the reduction of the hydrogen peroxide disinfectant; and controlling the generation of bubbles with the osmotic pressure adjusting agent which effervesces with the water of the aqueous solution to produce carbon dioxide bubbles which further block the perforations so that when the hydrogen peroxide disinfectant is totally reduced, the pH adjusting agent causes the resulting solution to have a pH between 6.8 and 7.4, which is isotonic with a tear of an eye, the reducing agent being in galenic form.

* * * * *